(12) United States Patent
Royalty

(10) Patent No.: US 8,231,518 B2
(45) Date of Patent: Jul. 31, 2012

(54) CARDIAC DIASTOLIC AUGMENTATION IMPROVING CARDIAC OUTPUT IN ELECTROMAGNETIC BIVENTRICULAR ASSIST DEVICE

(76) Inventor: John W Royalty, Crystal River, FL (US)

( * ) Notice: Subject to any disclaimer, the term of this patent is extended or adjusted under 35 U.S.C. 154(b) by 797 days.

(21) Appl. No.: 11/648,636

(22) Filed: Jan. 3, 2007

(65) Prior Publication Data

US 2007/0156008 A1    Jul. 5, 2007

Related U.S. Application Data

(60) Provisional application No. 60/755,413, filed on Dec. 31, 2005, provisional application No. 60/755,414, filed on Dec. 31, 2005, provisional application No. 60/755,415, filed on Dec. 31, 2005, provisional application No. 60/755,416, filed on Dec. 31, 2005, provisional application No. 60/755,424, filed on Dec. 31, 2005.

(51) Int. Cl.
*A61N 1/362* (2006.01)
*A61B 1/04* (2006.01)

(52) U.S. Cl. ......................... 600/16; 607/129
(58) Field of Classification Search ............... 600/16, 600/129
See application file for complete search history.

(56) References Cited

U.S. PATENT DOCUMENTS

| | | | |
|---|---|---|---|
| 5,498,228 A * | 3/1996 | Royalty et al. | 600/16 |
| 6,604,529 B2 * | 8/2003 | Kim | 128/899 |
| 6,887,192 B1 * | 5/2005 | Whayne et al. | 600/16 |
| 2004/0162463 A1 * | 8/2004 | Lau et al. | 600/37 |
| 2005/0160823 A1 * | 7/2005 | Zdeblick et al. | 73/715 |

\* cited by examiner

*Primary Examiner* — Nicole F Lavert
(74) *Attorney, Agent, or Firm* — Pillsbury Winthrop Shaw Pittman LLP

(57) ABSTRACT

An electromagnetic biventricular assist device adapted to assist ventricular output in a human heart includes a magnetic mat adapted for mounting inside a human body adjacent the heart, and an electromagnetic assembly adapted for mounting on the human body in functionally cooperative relation with respect to the mat. The mat is responsive to application of a first electromagnetic field generated by the electromagnetic assembly so as to be movable from a neutral position towards the heart and into compressive relation with the heart, and responsive to application of a second electromagnetic field that is opposite the first electromagnetic field so as to be movable from the neutral position in a direction away from the heart to expand ventricles in the heart and augment filling of the ventricles. A control circuit is constructed and arranged to control when the first and second electromagnetic fields are generated by the electromagnetic assembly.

11 Claims, 4 Drawing Sheets

CARDIAC DIASTOLIC AUGMENTATION IMPROVING CARDIAC OUTPUT IN ELECTROMAGNETIC BIVENTRICULAR ASSIST DEVICE

CROSS-REFERENCE TO RELATED APPLICATIONS

This application claims the benefit of priority from U.S. Provisional Patent Application Ser. Nos. 60/755,413, 60/755,414, 60/755,415, 60/755,416, and 60/755,424, all of which were filed Dec. 31, 2005, the contents of which are incorporated herein by reference in their entireties. The present application is related to U.S. patent application Ser. Nos. 11/648,914, 11/648,635, 11/648,637, and 11/648,908, all of which were filed on Jan. 3, 2007, and are incorporated herein by reference in their entireties.

BACKGROUND OF THE INVENTION

1. Field of the Invention

This invention relates to cardiac assist devices, and more particularly, to a device and method for assisting ventricular output in the human heart.

2. Description of Related Art

During the aging process, weakened or ineffective cardiac muscles may inhibit the cardiac pumping function from either the right, left, or both ventricles. When the pumping activity of the heart cannot meet the body's demands, systemic shock and subsequent organ dysfunction (such as pulmonary edema and renal failure) can result. Weakened heart muscles can also result in an over distended, dilated myocardium, which can have a detrimental effect on the electrical conduction and overall mechanical performance of the heart.

Advances in medical science have attempted to overcome these problems by replacing an impaired heart via heart transplants, or with devices such as artificial hearts. However, heart transplants are difficult to obtain since there is a limited donor supply. Moreover, artificial hearts have proved not entirely effective in duplicating cardiac contractions, are extremely expensive, and are known to be rejected by the human body.

Therefore, rather than replacing the heart, various arrangements have been proposed to assist right and left ventricular output of the existing impaired heart. For example, a number of arrangements are suggested in U.S. Pat. No. 4,621,617 to Sharma ("the '617 patent"). FIG. 1 of the '617 patent proposes an arrangement in which two components are disposed in surrounding relation to the heart and function to compress the heart therebetween to assist ventricular output thereof. The two components are furnished with electromagnetic induction circuitry, numerous pole elements, and are secured to one another by a mechanical hinge. It can be appreciated that the device is quite cumbersome, difficult to implant, and has achieved little if any acceptance. FIG. 4 of the '617 patent illustrates an alternate arrangement in which a compressor element is provided posteriorly to the heart and is movable to compress the heart against the rib cage. This embodiment is somewhat more practical, but nevertheless problematic in a number of respects. For example, no means are provided for evaluating the amount of compressive resistance or intra-cardiac pressure of the heart during compression thereof. As a result, the compressor element may either apply insufficient compressive force to the heart, thereby resulting in ineffective ventricular assist, or apply excessive compressive force, thereby damaging the heart. Additionally, providing a compressor element posteriorly to the heart requires complex surgery in which the entire chest cavity must be opened. Moreover, such placement of the compressor element is largely impractical since the aorta, esophagus and spine are all disposed in close proximity to the posterior portion of the heart and leave little room for insertion of any type of assist device.

An electromagnetic biventricular assist device, as described in U.S. Pat. No. 5,498,228, which is incorporated herein by reference in its entirety, includes a coil placed on the anterior surface of the chest of a human patient. When the coil receives current, a magnetic field is generated, which repels a magnetic mat that is located on the anterior surface of the heart posteriorly, thereby compressing the heart. These compressions are timed by a cardiogram so as to augment systole. The '288 patent does not discuss diastolic function. However, over the past 15 to 20 years, diastolic dysfunction has been found to result in major morbidity.

BRIEF SUMMARY OF THE INVENTION

It is an aspect of the present invention to provide a device and method for assisting cardiac diastolic function so as to improve overall cardiac performance in those patients suffering the morbidities of low cardiac output, e.g. recurrent pulmonary edema, hepatic congestion, and renal dysfunction.

In an embodiment of the present invention, an electromagnetic biventricular assist device that adapted to assist ventricular output in a human heart is provided. The assist device includes a magnetic mat adapted for mounting inside a human body adjacent the heart. The mat is made from a material responsive to application of a first electromagnetic field so as to be movable from a neutral position towards the heart and into compressive relation with the heart in response to application of the first electromagnetic field thereto, and responsive to application of a second electromagnetic field that is opposite the first electromagnetic field so as to be movable from the neutral position in a direction away from the heart. The assist device also includes an electromagnetic assembly adapted for mounting on the human body in functionally cooperative relation with respect to the mat, and for alternately generating the first electromagnetic field and the second electromagnetic field so that the mat alternately moves into the compressive relation with the heart and away from the heart so as to expand ventricles in the heart and augment filling of the ventricles. The assist device further includes a control circuit constructed and arranged to control when the first and second electromagnetic fields are generated by the electromagnetic assembly.

In embodiment of the present invention, a method for improving cardiac output augmentation performance of an electromagnetic biventricular assist device adapted to assist ventricular output in a human heart is provided. The electromagnetic biventricular assist device includes an electromagnetic assembly provided on an exterior surface of a human body, and a magnetic mat provided within the human body, anterior to the heart. The method includes generating a first electromagnetic field with the electromagnetic assembly, and moving the magnetic mat from a neural position towards a vertebral body so as to force the heart against the vertebral body and thereby compress the heart between the magnetic mat and the vertebral body in response to application of the first electromagnetic field to the mat. The method also includes generating a second electromagnetic field with the electromagnetic assembly. The second electromagnetic field is in an opposite direction as the first electromagnetic field. The method further includes moving the magnetic mat away from the neutral position so as to expand ventricles in the heart and augment filling of the ventricles in response to application of the second electromagnetic field to the mat.

These and other aspects and advantages of the invention will be apparent from the following description, the accompanying drawings, and the appended claims.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
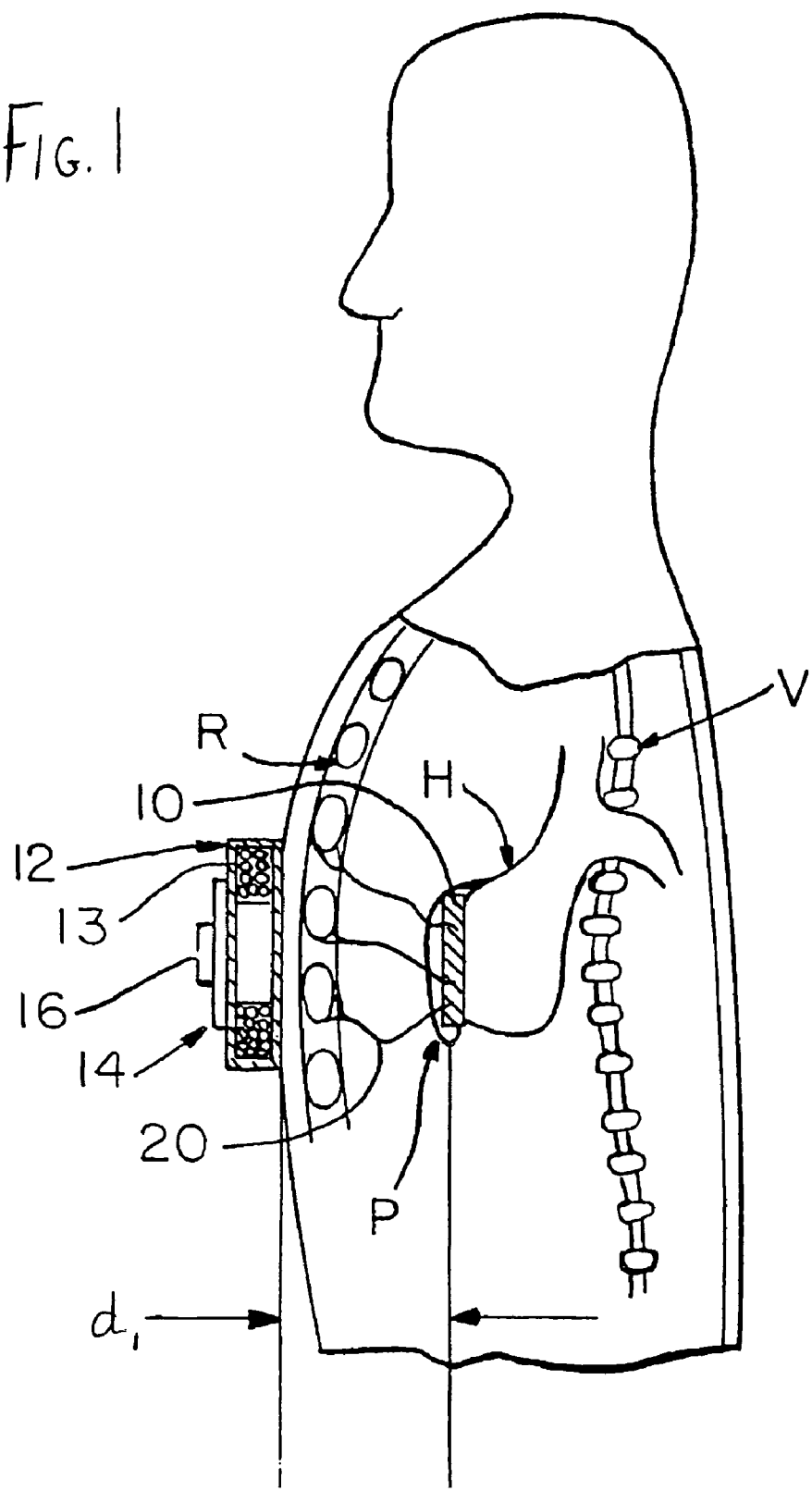
FIG. 1 is a side sectional view of a cardiac assist device according to an embodiment of the present invention shown inside a human body in a neutral relation with the heart.

FIG. 1 is a side sectional view taken through a human body and a cardiac assist device of an embodiment of the present invention, which is shown in a neutral relation with the human heart. "Neutral relation" as defined herein is a position in which the functioning of the heart is not affected by the cardiac assist device, i.e., the heart is not compressed by the device or expanded by the device, as will be discussed in greater detail below.

In the illustrated embodiment, the device includes a magnetic mat 10 which is adapted to be mounted inside the human body inside of the rib cage R, adjacent the heart H. Preferably, mat 10 is a permanent magnet made from a flexible ferromagnetic material, including but not limited to samarium cobalt, neodymium iron, and neodymium iron boron (NeFeBo). It can be appreciated, however, that the mat may comprise other materials (such as a superconductive material) so long as the mat is sufficiently responsive to application of an electromagnetic field to compress the heart in accordance with the principles of the present invention. Regardless of the material used, however, the exterior surface of the mat should be chemically inert, and not immunogenic, so that it does not react with blood, tissue, or organs. If necessary, the mat may be coated or surrounded by an inert substance, including but not limited to polyvinyl chloride (PVC), polytetrafluoroethylene (PTFE), or zinc.

The mat 10 is supported within the body, preferably in the space between the anterior aspect of the heart H and the posterior aspect of the pericardium P, although, as will be described later, the mat can also be positioned anteriorly to both the heart and pericardium. Preferably the mat support comprises a plurality of heavy mono-filament threads 20 each having one end secured to the mat and another end secured to the rib cage R (or sternum). The threads are flexible to permit movement of the mat, and should be sufficiently strong to withstand continued flexing without breakage. Where the mat is disposed between the heart and pericardium, the threads 20 are sutured through the pericardium. It can be appreciated that many alternatives to the mono-filament threads can be used to support the mat, as long as such alternatives maintain the mat in movably supported relation, anteriorly and proximate to the heart.

An electromagnetic assembly 12 is adapted to be mounted externally on the human body, preferably on the chest, in functionally cooperative relation with respect to the mat 10. When the mat 10 is in a neutral relation with the heart, as shown in FIG. 1, the distance between the electromagnetic assembly 12 and an anterior surface of the mat 10 may be represented by $d_1$.

Figure 2:
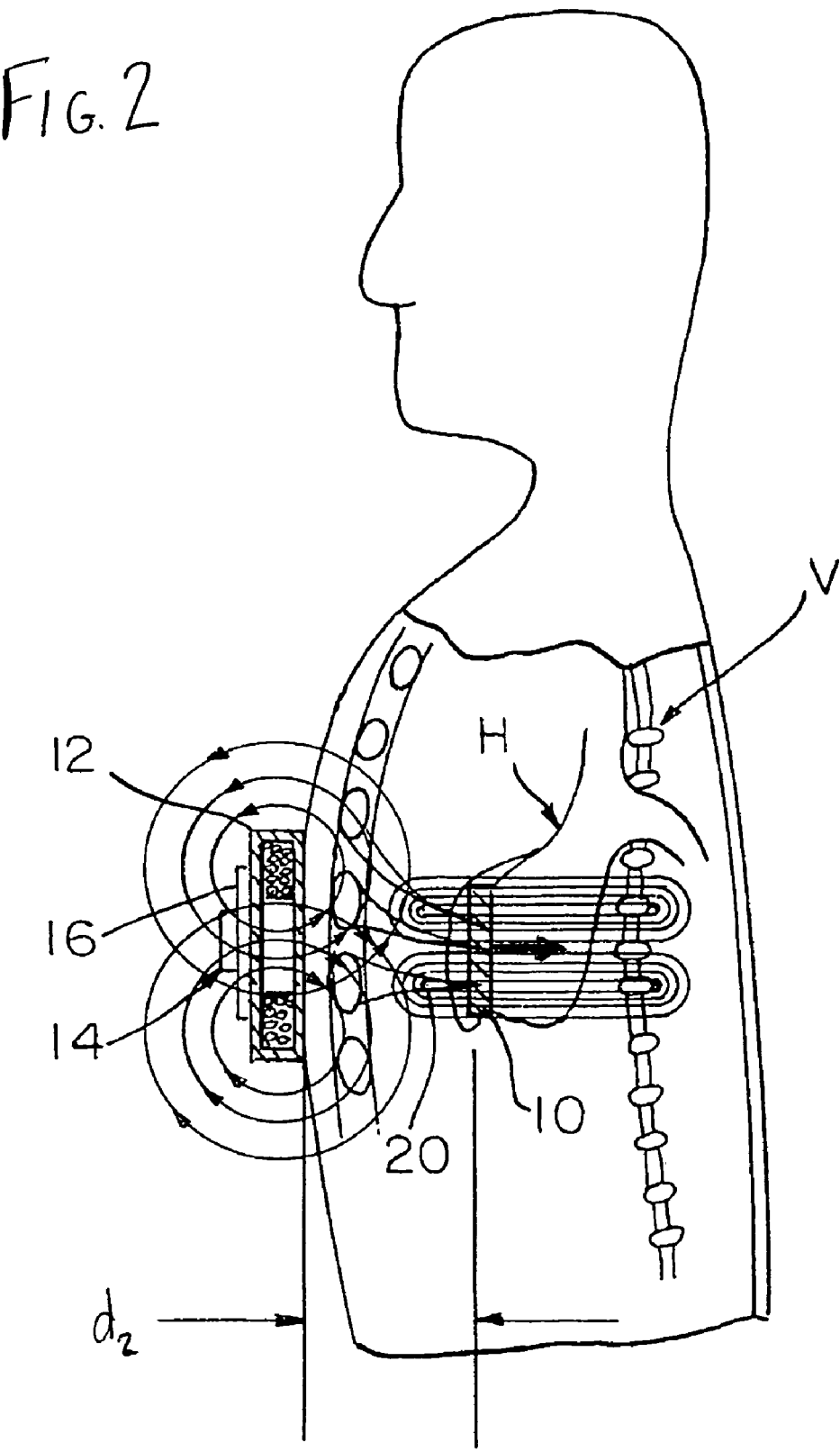
FIG. 2 is a side sectional view of the cardiac assist device of FIG. 1 shown inside the human body in a compressive relation with the heart.
Figure 3:
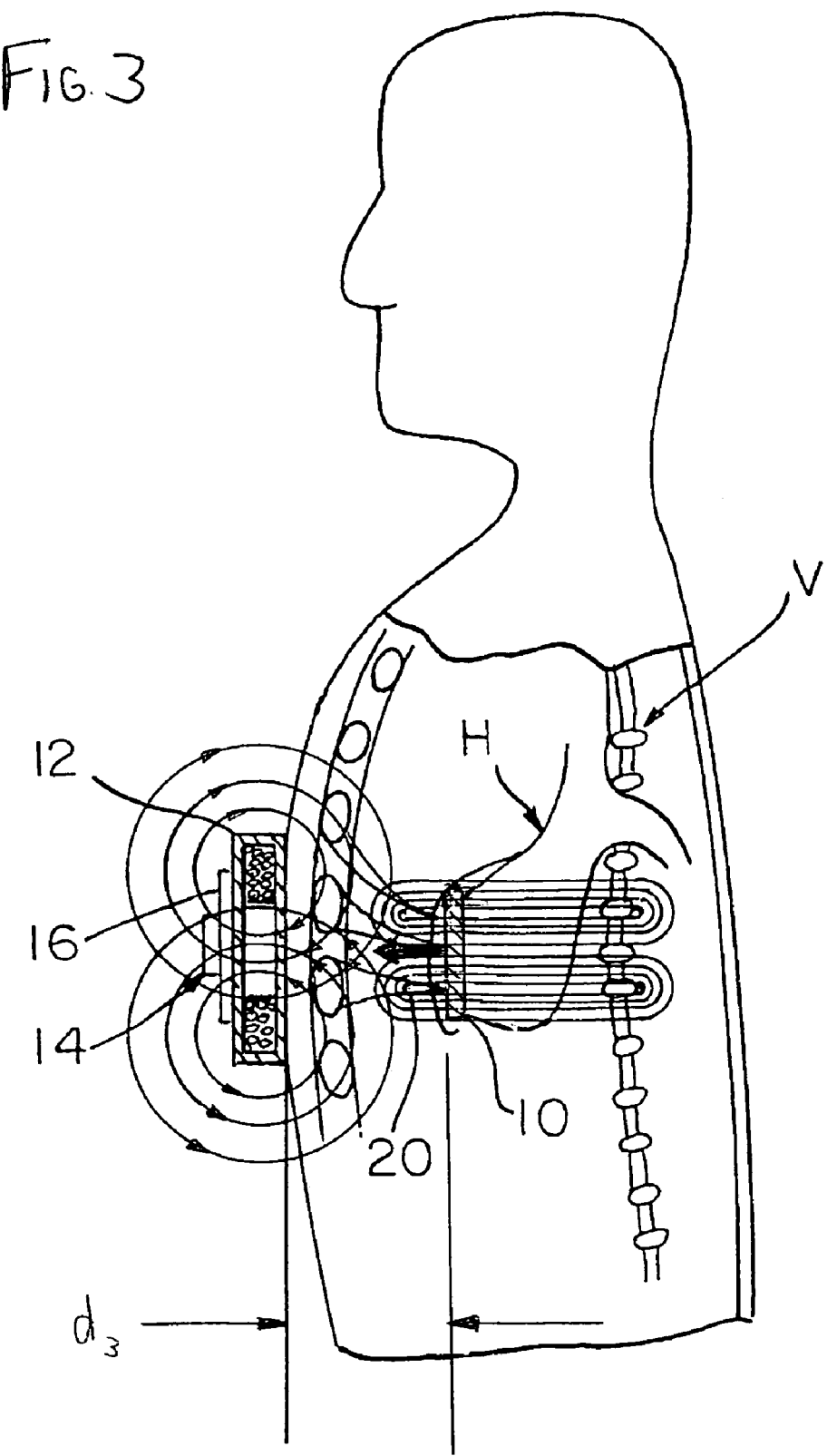
FIG. 3 is a side sectional view of the cardiac assist device of FIG. 1 shown inside the human body in an expansive relation with the heart.

The electromagnetic assembly 12 includes an inductive coil 13 to which a current may be supplied in a first direction (preferably by a D.C. battery, not shown) to produce a first electromagnetic field, which repels the mat into compressive relation with the heart, as shown in FIG. 2. When the mat 10 is in compressive relation with the heart, the distance between the electromagnetic assembly 12 and an anterior surface of the mat 10 may be represented by $d_2$, which is greater than $d_1$. The electromagnetic assembly 12 is also configured to supply a current to the coil 13 in a second direction, which is opposite the first direction, to produce or generate a second electromagnetic field, as shown in FIG. 3. The second electromagnetic field is configured to attract the mat 10 such that the mat is in an expansive relation with, i.e. pulls on, the heart. When the mat 10 is in expansive relation with the heart, the distance between the electromagnetic assembly 12 and an anterior surface of the mat 10 may be represented by $d_3$, which is less than $d_1$. As the mat 10 moves from the neutral position in a direction that is away from the heart, the heart may expand so as to expand the ventricles in the heart, which may augment the filling of the ventricles.

More particularly, electromagnetic assembly 12 alternately generates the first and second electromagnetic fields to alternately compress the heart against vertebral body V (e.g., the spine) and expand the heart, thereby assisting the mechanical pumping function of the heart during both systolic and diastolic functions. The magnitude of the force produced by the electromagnetic assembly on the mat will be proportionally dependent on the mat's magnetic field strength, the amount of current traveling through the electromagnetic assembly 12, and the number of current-turns in the electromagnetic assembly 12, but inversely proportional to the distance between the electromagnetic assembly and the mat.

Figure 4:
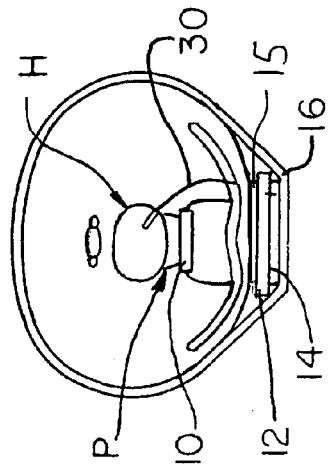
FIG. 4 is a top sectional view showing a cardiac assist device of another embodiment of the present invention inside the human body.

A first transducer 14 (preferably a load cell, force gauge type, made from piezo AC material) is secured to the electromagnetic assembly 12 on the side opposite the chest by a preferably rigid harness 16, and a second transducer 15 (again, preferably a load cell, force gauge type, made from piezo AC material) is secured to the electromagnetic assembly on the same side as the chest. The harness is disposed in surrounding relation to the human torso as shown in FIG. 4, which is a top sectional view through the torso. The harness 16 may include shoulder straps to prevent vertical movement of the electromagnetic assembly 12 when an individual is in the upright position.

In FIG. 4, the mat as shown is positioned anteriorly to both the heart and pericardium. It can be appreciated, however, that it is more preferable to position the mat in the natural space between the heart and pericardium to enable the mat to more effectively compress the heart by being in direct contact therewith. In addition, placement of the mat anteriorly to the pericardium is more difficult since a significant amount of body tissue between the pericardium and sternum must be removed to enable such placement.

Figure 5:
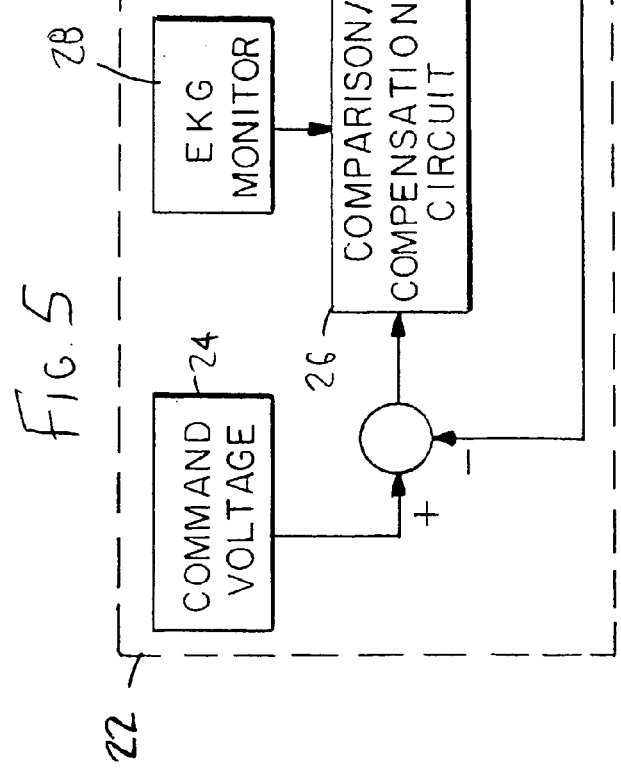
FIG. 5 is a block diagram schematically showing the interrelation of various components of the cardiac assist device of FIG. 1.

As shown in FIG. 5, the transducers form part of an electronic feedback/control loop, and function to evaluate the compressive resistance of the heart during movement of the mat into compressive relation with the heart, and the expansive resistance of the heart during movement of the mat into expansive relation with the heart. More specifically, when the electromagnetic assembly 12 generates the first electromagnetic field to repel the mat 10, an equal and opposite force is applied to the electromagnetic assembly, thus repelling the assembly away from the chest. It can be appreciated that when such an electromagnetic field is generated, the pressure transducer 14 is compressed between the assembly 12 and harness 16 (e.g., see FIG. 2). The transducer 14 senses the compressive pressure or force applied thereto and outputs a voltage proportional to such force or pressure. A control circuit 22 receives the signal generated by the transducer and controls the intensity of the first electromagnetic field generated by the electromagnetic assembly as a function of that signal. As a result, the control circuit effectively controls the degree to which the mat compresses the heart.

Similarly, when the electromagnetic assembly 12 generates the second electromagnetic field to attract the mat 10, an equal force is applied to the electromagnetic assembly 12, thus attracting the assembly toward the chest. It can be appreciated that when such an electromagnetic field is generated, the pressure transducer 15 is compressed between the assembly 12 and the chest. The transducer 15 senses the compressive pressure or force applied thereto and outputs a voltage proportional to such force or pressure. A control circuit 22 receives the signal generated by the transducer and controls the intensity of the second electromagnetic field generated by the electromagnetic assembly as a function of that signal. As a result, the control circuit effectively controls the degree to which the mat expands the heart.

More specifically, control circuit 22 includes a compensation/comparison circuit 26 (or "compensation circuit") which compares the voltage generated by the transducers 14, 15 to a command voltage generated by command voltage generator 24. The command voltage corresponds to a predetermined voltage which represents the ideal amount of force required to compress and expand the heart. The compensation/comparison circuit 26 measures the difference between the voltages generated by the pressure transducers 14, 15 and the command voltage, and then digitally compensates for such difference so that an appropriate amount of current is sent through the coil in the electromagnetic assembly 12. For example, if the voltage generated by the respective transducer 14, 15 is less than the command voltage, the compensation circuit 26 will ramp up the current sent through the coil 13 and thereby increase the intensity of the magnetic field applied by electromagnetic assembly 12. In contrast, if the voltage generated by the respective transducer 14, 15 is less than the command voltage, the compensation circuit will decrease the amount of current through the coil 13 and thereby decrease the intensity of the magnetic field applied by the electromagnetic assembly 12. Thus, the intensity or magnitude of the first and electromagnetic fields generated by the electromagnetic assembly 12 is controlled so that the compressive force applied by the mat 10 to the heart remains within a predetermined range with each compressive stroke, and the tensile force applied by the mat 10 to the heart remains within a predetermined range with each expansive stroke.

The predetermined amount of force to be applied to the heart in order to obtain the desired cardiac output is determined experimentally during an initial procedure wherein a catheter, such as the Swan-Ganz catheter, is placed in the heart to monitor intra-ventricular pressures. This type of catheter is also capable of measuring actual cardiac output. The cardiac output and intra-cardiac pressure are correlated with the voltages generated by the pressure transducers 14, 15, and after several days of experimentation, the Swan-Ganz catheter may be removed. The pressure transducers 14, 15 thereafter generate voltages as a function of the compressive and expansive resistances of the heart, which in turn are a function of either the intra-cardiac pressure or output of the heart.

It can be appreciated that the Swan-Ganz catheter may be kept within the heart and utilized as a transducer in lieu of the transducers 14, 15. Such an arrangement is shown in FIG. 4, wherein a Swan-Ganz catheter 30 is in place. It is advantageous, however, to remove the Swan-Ganz catheter since use thereof requires the provision of wires extending through the human flesh from the catheter to the electromagnetic assembly 12 and control circuit. This may be quite uncomfortable for the subject.

While the magnitude of the first and second electromagnetic fields generated by electromagnetic assembly 12 is controlled by the control circuit 22 together with the pressure transducers 14, 15 it can be appreciated that the frequency of the first and second electromagnetic fields must coincide with the natural contractions and expansions of the heart. This may be accomplished by use of an electrocardiogram (EKG) 28 monitor integrated into the control circuit. The EKG monitor measures the electrical activity of the heart and, together with the rest of the control circuit, functions to synchronize the first electromagnetic field generated by the electromagnetic assembly with the QRS spike of the electrocardiogram. This technique of adjusting the rate at which the mat compresses the heart is similar to that used in intra-aortic balloon pumps, and is conventional in this field of technology. The application of the first electromagnetic field may be specifically timed during systole and determined in a custom manner for each patient with regard to the duration of the compression, the change in pressure as a function of change in time in the specific time interval relative to the QRS wave or systolic segment. These three variables may be optimized, as determined by the best cardiac output during the initial phase devise treatment.

The current supplied to the coil 13 of the electromagnetic assembly 12, which sits on the anterior aspect of the chest, may be reversed during diastole in an effort to improve diastolic filling of the ventricles. As discussed above, this results in a polarity switch of the electromagnet and instead of repelling the magnetic mat as previously described and shown in FIG. 2, the magnetic mat is drawn towards the sternum and away from the anterior aspect of the heart, as shown in FIG. 3. Because of the uniform apposition of the anterior aspect of the heart to the posterior aspect of the magnetic mat (which may be further enhanced by the custom manufacture of each magnetic mat per patient, as described in U.S. Provisional Patent Application Ser. No. 60/755,424, which is incorporated herein by reference, and U.S. patent application Ser. No. 11/648,635 (published as U.S. Patent Application Publication. No. 2007-0156007 A1), which is incorporated herein by reference), significant suction and negative pressure may take place between the anterior aspect of the heart and the posterior aspect of the magnetic mat. As the ribs of the patient's chest move laterally and superiorly with each inspiration, significant negative pressure may take place between the rib cage and the lung parenchyma. This may result in an expansion of the lung tissue.

In a similar fashion, as the magnetic polarity of the coil is reversed, the magnetic mat is drawn anteriorly, and due to the negative pressure between the magnet in the anterior surface of the heart over the ventricles, the ventricles expand. As the ventricles expand, ventricular filling is augmented, and evacuation of the atrium and atrial emptying may occur. The quicker the pressure in the venous tree can be reduced, and the further the right heart and venous pressure can be reduced, the easier it should be for the arterial blood to perfuse the extremities and deliver oxygen. This may also decrease the risk for hepatic congestion. Although there is significant resistance produced by the venous tree, the resistance may be changed, which may improve the diastolic function of the heart.

As a general rule, when the diastolic function of the heart improves, cardiac output improves. Just as the systolic augmentation (i.e., compression of the heart) is dependent on timing onset, duration, and the pressure curve actuation in improving systolic ejection fraction, diastolic augmentation is dependent on accurate time onset, duration segment, and pressure curve actuation. The signal provided by a cardiogram, such as an EKG may be used to assist in the timing of the current reversal and generation of the second magnetic field.

The preferred procedure for inserting the mat 10 into the human body in cooperative relation the heart will now be described. The heavy mono-filament threads 20 each have one end thereof secured to the peripheral edges of two opposite sides of the mat, which preferably has a substantially rectangular or oval shape. An incision is made immediately below the breastbone using the sub-xiphoid approach, and the threads are then sutured to the rib cage and/or sternum by use of curved trochar sheath. The sutures are passed anteriorly to the epicardium, but posterior to the anterior aspect of the pericardium, and exit intercostally lateral to the sternum. Enough slack should be left in the mono-filament sutures to permit movement of the mat 10 away from the electromagnetic assembly 12 into compressive relation with the heart upon application of the electromagnetic fields.

It will be appreciated that the aspects of this invention have been fully and effectively accomplished. It will be realized, however, that the foregoing preferred specific embodiments have been shown and described for the purpose of this invention and is subject to change without departure from such principles. Therefore, this invention includes all modifications encompassed within a spirit and scope of the following claims.

What is claimed is:

1. An electromagnetic biventricular assist device adapted to assist ventricular output in a human heart, comprising:
   a magnetic mat adapted for mounting inside a human body adjacent the heart so as to be in a uniform apposition with the heart, said mat being made from a material responsive to application of a first electromagnetic field so as to be movable from a neutral position towards the heart and into compressive relation with the heart in response to application of the first electromagnetic field thereto, and responsive to application of a second electromagnetic field that is opposite the first electromagnetic field so as to be movable from the neutral position in a direction away from the heart; and
   an electromagnetic assembly adapted for mounting on the human body in functionally cooperative relation with respect to said mat, and for alternately generating the first electromagnetic field and the second electromagnetic field so that said mat alternately moves into said compressive relation with the heart and away from the heart so as to create suction and negative pressure between the heart and the mat to expand ventricles in the heart and augment filling of the ventricles; and
   a control circuit constructed and arranged to control when the first and second electromagnetic fields are generated by said electromagnetic assembly.

2. The electromagnetic biventricular assist device according to claim 1, wherein said electromagnetic assembly comprises an inductive coil, and wherein said control circuit is configured to control an amount and direction of current that travels through said coil, the amount of current that travels through said coil being proportional to an intensity level of the first and second electromagnetic field generated by said electromagnetic assembly.

3. The electromagnetic biventricular assist device according to claim 2, wherein the first electromagnetic field is generated when the current flows in a first direction, and the second electromagnetic field is generated when the current flows in a second direction that is opposite to the first direction.

4. The electromagnetic biventricular assist device according to claim 3, wherein said control circuit comprises a cardiogram monitor for generating signals as a function of electrical activity of the heart, said signals being used to determine the direction and amount of flow of the current to the electromagnetic assembly to alternately generate the first electromagnetic field and the second electromagnetic field so that said mat alternately moves into and out of said compressive relation with the heart, and further away from the heart, as a function of the electrical activity of the heart.

5. The electromagnetic biventricular assist device according to claim 4, wherein the cardiogram monitor is an electrocardiogram monitor.

6. The electromagnetic biventricular assist device according to claim 1, further comprising a harness for mounting said electromagnetic assembly means on the human body.

7. The electromagnetic biventricular assist device according to claim 6, further comprising a transducer for evaluating compressive resistance of the heart during movement of said mat into compressive relation with the heart and for generating an electrical signal as a function of said compressive resistance of the heart.

8. The electromagnetic biventricular assist device according to claim 7, wherein said transducer is compressed between said harness and said electromagnetic assembly, and wherein compressive force applied to said transducer enables said transducer to generate said signal as a function of the compressive resistance of the heart.

9. The electromagnetic biventricular assist device according to claim 8, wherein said transducer comprises a load cell force gauge.

10. The electromagnetic biventricular assist device according to claim 9, wherein said signal generated by said transducer is a voltage proportional to the compressive resistance of the heart, and wherein the control circuit comprises a compensation circuit for comparing a command voltage to said proportional voltage and for adjusting the amount of current that travels through said coil as a function of a difference between said command and proportional voltages.

11. The electromagnetic biventricular assist device according to claim 7, further comprising a second transducer for evaluating expansive resistance of the heart during movement of said mat into expansive relation with the heart and for generating an electrical signal as a function of said expansive resistance of the heart.

* * * * *